United States Patent
Divo et al.

(10) Patent No.: US 9,033,496 B2
(45) Date of Patent: May 19, 2015

(54) METHOD OF MEASURING MORPHO-GEOMETRICAL PARAMETERS OF A PERSON WEARING EYEGLASSES

(75) Inventors: Fabien Divo, Charenton-le-Pont (FR); Philippe Pinault, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 165 days.

(21) Appl. No.: 13/561,474

(22) Filed: Jul. 30, 2012

(65) Prior Publication Data

US 2013/0188128 A1 Jul. 25, 2013

(30) Foreign Application Priority Data

Sep. 28, 2011 (FR) ...................................... 11 58665

(51) Int. Cl.
- *A61B 3/10* (2006.01)
- *A61B 3/14* (2006.01)
- *A61B 3/18* (2006.01)
- *G02C 13/00* (2006.01)

(52) U.S. Cl.
CPC ................. *A61B 3/18* (2013.01); *G02C 13/005* (2013.01)

(58) Field of Classification Search
USPC .......... 351/200, 204–206, 209–211, 221–223
See application file for complete search history.

(56) References Cited

U.S. PATENT DOCUMENTS

| 6,257,721 B1 | 7/2001 | Hayashi et al. |
| 2010/0195045 A1* | 8/2010 | Nauche et al. ............... 351/204 |

FOREIGN PATENT DOCUMENTS

| WO | 9901791 | 1/1999 |
| WO | 9903278 | 1/1999 |

OTHER PUBLICATIONS

International Search Report dated Apr. 3, 2012.

* cited by examiner

*Primary Examiner* — Scott J Sugarman
*Assistant Examiner* — Brandi Thomas
(74) *Attorney, Agent, or Firm* — Sofer & Haroun, LLP

(57) ABSTRACT

A method of measuring morpho-geometrical parameters of a person wearing eyeglasses includes causing the person to observe a point situated in front at infinity while holding the head naturally on a direction (24) that is substantially horizontal, acquiring a first image of the position of the frame (21) in this first posture, causing the person to observe the target (8, 18) placed in a known position relative to the image acquisition system, by adopting a position that is natural and comfortable and that involves at least a tilting movement of the head; acquiring a second image of the position of the frame (21) in this second posture, determining the positions of the eyes (27) from one of the two images, computer processing of the two images obtained in order to determine the morpho-geometrical parameters of the person, and delivering the results of the measurements.

16 Claims, 4 Drawing Sheets

METHOD OF MEASURING MORPHO-GEOMETRICAL PARAMETERS OF A PERSON WEARING EYEGLASSES

RELATED APPLICATION

This application claims the benefit of priority from French Patent Application No. 11 58665, filed on Sep. 28, 2011, the entirety of which is incorporated by reference.

BACKGROUND

1. Field of the Invention

The technical field of the invention relates to methods of measuring morpho-geometrical parameters of a person wearing eyeglasses. By way of example these parameters may include the pupillary distance PD, the height H between the pupil and the bottom edge of the lens, the pantoscopic angle ΘP, i.e. the angle of inclination of the lenses relative to the facial plane of the person, the distance DVO between the eye and the lens V, and also the center of rotation CRO of the eye. It is essential to know these parameters in order to personalize a pair of eyeglasses properly, in particular with progressive lenses.

2. Description of Related Art

Methods also exist enabling some of these morpho-geometrical parameters to be measured. A first category of such methods make use of a vertical measurement column of large size with a camera being adjusted to the height of the eyes, the person wearing the eyeglasses looking at their own reflection in a mirror. That type of equipment is very bulky and thus requires premises of large size for taking the measurements, and it is not very flexible in use insofar as it cannot be moved easily in order to refine measurement, nor can it be broken up into separate elements in order to adapt to a given situation.

A second category of methods involves equipment of smaller size, in particular suitable for being placed on a table, but requiring a measurement protocol and positioning of the person wearing the eyeglasses that are most constraining. That type of method requires the person to adopt a very particular position for the head, and requires a clip to be applied to the eyeglass frame, the clip being provided with a rocker beam. A first step then consists in causing the person to adopt a natural posture, with the rocker beam then being blocked so as to fix the angle between the clip and the rocker beam, this angle corresponding to the pantoscopic angle. During a second step, the person wearing the eyeglass frame and its clip looks at a camera arranged above a screen. The person needs to tilt the head so that the blocked rocker beam is perpendicular to the axis joining the eyes and the camera. Such a method requires adjustments that are complex and accurate, and it requires a certain amount of dexterity on the part of the person wearing the eyeglasses, in order to be capable of taking up the correct position relative to the camera axis and to fix the position of the rocker beam accordingly.

OBJECT AND SUMMARY

The methods of the invention for measuring morpho-geometrical, parameters make use of equipment that is flexible in use capable easily and quickly of taking measurements of said parameters that are accurate and reliable, while not imposing any constraints on the person wearing eyeglasses. Throughout the method, the person need only adopt postures that are comfortable, holding the head in natural manner, without ever needing to adopt a series of postures that require accurate positioning and inclination or pivoting of the head, and without any need to be fitted with specific equipment. The methods of the invention are also designed to give the results of the measurements automatically and quickly.

The invention provides a measurement method for measuring morpho-geometrical parameters of a person wearing eyeglasses, said method implementing an independent computer device having a screen, a target, a compact image acquisition system including means for determining its angle of inclination, said system being connected to said screen, and a computer enabling the image acquisition system to be controlled and enabling the images obtained to be processed. The main characteristic of the method of the invention is that it comprises the following steps:

causing the person to observe a point situated in front and at infinity while holding the head naturally in a substantially horizontal direction, the pair of eyeglasses occupying a natural position on the person's face;

acquiring a first image or the position of the frame in this first posture;

causing the person to observe the target placed in a known position relative to the image acquisition system, by adopting a position that is natural and comfortable, said observation causing the person's head to be moved in tilting, the pair of eyeglasses conserving an unchanged position on the person's face relative to the first posture;

acquiring a second image of the position of the frame in this second posture, by means of the same image acquisition system as was used for the first posture;

determining the positions of the eyes from one of the two images;

computer processing of the two images obtained in order to determine the morpho-geometrical parameters of the person from the positions of the eyes, from the position of the frame in the first posture, from the position of the frame in the second posture, and from the angle of inclination of the image acquisition system, said processing including a calculation correction to take account of a difference in inclination of the plane of the person's face relative to the gaze axis from the eyes to the gaze point, between the first and second positions; and providing the results of the measurements.

The principle of such a method relies on the wearer of eyeglasses adopting two postures that are natural and comfortable, and then on acquiring two images of the eyeglass frame corresponding to those two postures, and finally on computer processing of those two images in order to deduce the desired morpho-geometrical parameters therefrom. The image acquisition system may comprise at least one camera for taking moving or still pictures. It should be specified that the image acquisition system is the same for acquiring both images in the two postures. The angle of inclination of the axis of the image acquisition system must be known accurately in particular in order to be able to correct parallax errors due to the angle of inclination. The image acquison system may be used either in stationary manner, with a given angle of inclination, or else in movable manner over a range of possible angles of inclination. In the first configuration, it is the wearer who changes position so as to ensure that the wearer's face appears in the center of the field of the camera. In the second configuration, the angle of inclination of the acquisition system is adapted to the position of the person so as to ensure the person's face is properly framed. The term "compact" when applied to the image acquisition system means that said system is of small size and can be easily handled so as to be placed on a conventional piece of furniture such as a table or a desk, and so as to be inclined at an appropriate angle. Advantageously, the target is carried by the image acquisition system. In this way, the equipment needed for implementing a method of the invention is less dispersed. In another preferred implementation of the measurement method of the invention, the target is constituted by the image acquisition system itself. The images taken by the acquisition system in the two postures show mainly the eyeglass frame positioned relative to the eyes of the person. All of the information needed for computer processing the images in order to obtain the looked-for parameters must appear clearly in said images as a result of the position of said eyeglass frame in three dimensions relative to the person's eyes. It is fundamental for both the frame and the person's eyes to appear clearly and accurately in the images. In a method of the invention, the position of the eyeglasses frame on the person's face remains constant between the first and second postures. Once properly positioned on the face, the position of the eyeglasses is not readjusted from one position to the other. The morpho-geometrical parameters can then be deduced easily from said images on the basis of conventional trignometrical relationships. It is important to mention that the image processing includes calculating corrections for the parameters obtained in order to take account of the plane of the face being positioned differently relative to the sighting axis between the person's eyes and the gaze point in the first and second postures. Although this difference is small, being of the order of a few degrees, the consequences on the values for the parameters that are to be determined can generally be significant. The frame may optionally be provided with position-identifying means in the form of a clip provided with markers so as to enable its orientation in three dimensions and its angle of inclination to be viewed accurately in an image. The main function of the screen is to enable the acquired images to be viewed while the person is adopting the two postures. It may also serve to deliver the result of the measurements of the looked-for morpho-geometrical parameters. The method may be controlled either directly by the person wearing the eyeglasses, or else by an operator who may be an optician. In order to avoid any ambiguity in the description, the terms "pair of eyeglasses" and "frame" should be considered as being equivalent. The term "tilting" is used of a movement of the head that is a front-to-back pivoting movement of the head about a horizontal axis. A method of the invention serves to facilitate measurement steps for the purpose of proposing a realistic approach to different real observation situations on the part of a person. The parameters determined by such a method are thus subject to less random error than parameters determined for the most part by theoretical calculation.

Advantageously, the frame is fitted with position-identification means in the form of a clip provided, with markers and fastened on said frame, the angle of inclination of said frame being evaluated from a single camera. The clip carrying markers enables the angle of inclination of the frame on the person's face to be viewed accurately. Under such circumstances, only one camera is needed in order to determine this angle of inclination from the dimensional characteristics of said clip in the image captured by the camera it is assumed that said camera forms an integral portion of the image acquisition system implemented in the method of the invention.

In another preferred embodiment of the method of the invention, the angle of inclination of the frame is evaluated by means of at least one camera used in a stereoscopic method, said camera taking two images. The camera takes two images in which a reference element appears, which element may equally well be placed on the person's face or on a wall behind the person, said images serving to determine the angle of inclination of the frame.

Preferably, the angle of inclination of the frame is evaluated by means of at least two cameras used in a stereoscopic method. In this configuration, at least two distinct cameras placed at at least two different locations and each taking pictures of the frame serve to determine the angle of inclination of said frame without having recourse to a clip carrying marking.

Advantageously, the image acquisition system is a high-resolution camera. Typically, a high-resolution camera is a camera having resolution greater than 1 mega pixel. The greater the resolution of the camera, the more satisfactory the accuracy of the measurements.

Preferably, the means for determining the angle of inclination of the acquisition system comprise an inclinometer. A priori, the image acquisition system remains fixed in a given position. However for people of very large size, it may be found necessary to tilt the image acquisition system in order to obtain a satisfactory image of the person's eyes and eyeglass frame. The angle of inclination needs to be known in order to be incorporated subsequently in the calculation of the parameters derived from the measurements.

Preferably, the morpho-geometrical parameters measured by said method are the height H between the pupil and the bottom rim of the lens V, and the pantoscopic angle $\Theta P$. It should be recalled that the pantoscopic angle corresponds to the angle of inclination of the lenses V relative to a vertical plane when the frame is placed on the person's nose and the person is gazing in the distance.

Advantageously, the measured height Hm is corrected in order to take account of the distance DVC) between the lens V and the eye.

Preferably, the distance PVC) between the lens and the eye is deduced from a measurement of disparities between the two images. The two images taken while the person is adopting the two different postures make it possible to calculate the distance between the lens and the eye. This distance DVO is another morpho-geometrical parameter that can be measured with a measurement method of the invention.

Preferably, an operator is placed in front of the person wearing eyeglasses, said operator adjusting the image acquisition system and controlling the various steps of the measurement method of the invention. The method may be implemented by an optician in order to obtain a measurement of the morpho-geometrical parameters of a person wearing eyeglasses. The optician thus operates the image acquisition system as convenient in order to obtain a usable image of the person's eyes and the frame in both postures. For this purpose, the screen is directed to face the optician who views said images in real time. It is also the optician who triggers picture taking and who launches image processing by the computer. P measurement method of the invention has been developed mainly for use on the premises of an optician.

Advantageously, the acquisition system is adjusted in angle of inclination in order to adapt to the position of the person's face. For this configuration, the acquisition system is moved by varying its angle of inclination in order to obtain a properly framed image of the person's face.

In another preferred implementation of the measurement method of the invention, the angle of inclination of the acquisition system is constant, the person positioning the face at the appropriate height for causing it to appear in the center of the image. It can happen that the image acquisition system is not adjustable in angle of inclination. Under such circumstances, the acquisition system is fixed in a given position and it is, the person's face that is moved so as to bring it into the center of the field of said acquisition system. In this configuration, the person is subjected to a few prior positioning constraints in order to combine the conditions needed for obtaining measurements that are accurate and reliable.

The invention also provides a measurement device for implementing a measurement method of the invention. The main characteristic of a device of the invention is that it comprises a computer, at least one camera fitted with an inclinometer, and a display screen enabling the images taken by said camera to be viewed together with she results of the measurements, it being possible for the position of the camera and the position of the screen to be adjusted independently of each other. This measurement device can be thought of as a measurement kit in which the various parts are connected to one another in order to interact and provide the desired measurements, without necessarily requiring any particular and constraining arrangement. This type of device presents a certain amount of flexibility as to how it is connected together, and can thus easily be installed in any type of environment, whether on a table or a desk or merely on the ground. The ability to adjust the position of the screen independently to the position of the camera enables the measurement device of the invention to be used in multiple configurations and makes it possible to increase the performance of a measurement method of the invention by positioning the various pieces of equipment required for implementing said method in a manner chat is as accurate as possible.

Advantageously, the measurement device is constituted by a tablet combining the screen, a secondary camera, an inclinometer, and she computer, and also by said at least one camera fitted with its in clinometer. This version of the device is one of the more compact versions, and can therefore be installed in a small space. By grouping together the various component parts of the device in a tablet of small size, the measurement device is made even more flexible in use since a person or an operator can control all of the method from a single piece of kit and perform the necessary adjustment without any need to move about or to move the parts relative to one another. It should be assumed that a tablet is an article of small dimensions that are compatible with being handled easily by a person or an operator. This type of article may in particular be moved easily by hand in a room so as to be installed at an accurate location and pointed in the desired direction. The tablet may have a touch screen or it may be used more conventionally with the help of a mouse. The camera may be fastened directly to the tablet or else to a support that is also used for supporting the tablet.

Preferably, the device includes a support on which the tablet and the camera are fastened. The support enables the device to be made more compact by enabling the camera to be placed very close to the tablet, with the distance between these two elements being less than a few centimeters.

Preferably, the camera and the tablet are situated on either side of a vertical plane and form between them an angle lying in the range 15° to 45°. Advantageously, this angle is 30°. In this way, the screen is oriented in a certain direction and the camera is oriented in an opposite direction. This arrangement allows an optician to observe the face of a person wearing eyeglasses directly on the screen of the tablet, with the image being picked up by the camera placed at the back of said tablet. In this configuration, the optician is not obliged to place the camera at the same height as the person's face in order to acquire an image. It can suffice to place the measurement device on a table or a desk and then adjust the angle of inclination of the tablet and camera as accurately as possible.

The methods of the invention for measuring morpho-geometrical parameters of a person present the advantage of being particularly ergonomic and user-friendly, insofar as the person wearing eyeglasses does not need to carry any particular equipment and does not need to adopt a series of constraining and repetitive postures. They also have the advantage of giving the results of the measurements immediately to the person or to the optician, either via a screen, or else by means of a printed document. Finally, the measurement device implemented in a method of the invention is of small size and can Therefore be installed in a room of small volume, on a table or on a desk.

BRIEF DESCRIPTION OF THE DRAWINGS

There follows a detailed description of a preferred implementation of the measurement method of the invention given with reference to FIGS. 1 to 9.

DETAILED DESCRIPTION

Figure 1:
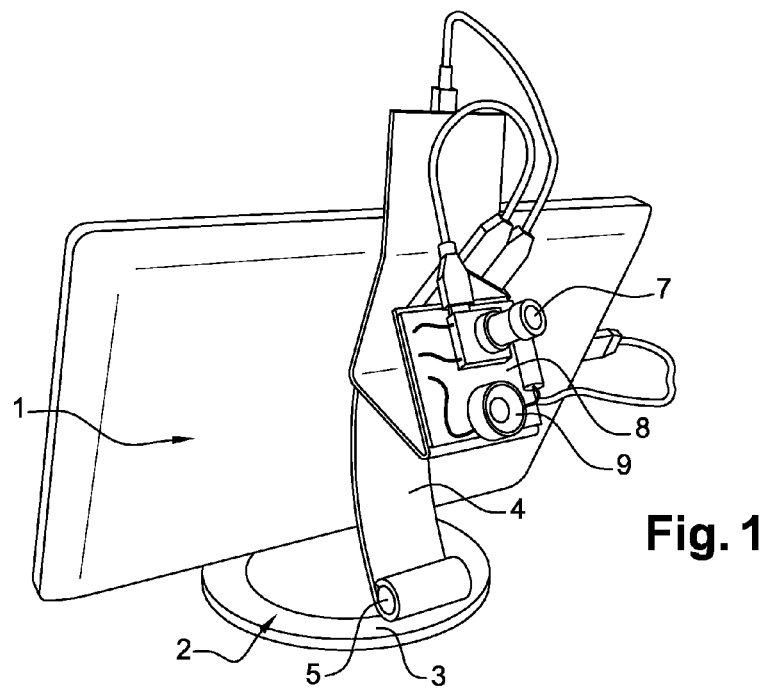
FIG. 1 is a perspective view of a first preferred embodiment of a measurement device enabling a method of the invention to be implemented.

With reference to FIG. 1, a first preferred embodiment of a measurement device for implementing a method of measuring morpho-geometrical parameters of a person wearing eyeglasses is constituted by a tablet 1 comprising a screen and a computer, standing on a support 2 enabling it to be stood on a surface that is plane and horizontal. The support 2 comprises a wide circular stand 3 extended by a support rod 4 that is hinge-mounted on said stand 3 about a pivot axis 5. In other words, when the stand 3 is standing on a horizontal surface 6 the rod 4 is in a position that is inclined to a greater or lesser extent relative to the vertical direction. The rod 4 may be considered as a metal strip of small thickness. The tablet 1 rests on the stand 3 while leaning against the rod 4. An image acquisition system 7 in the form of a high-resolution video camera, advantageously having resolution greater than or equal to 1 million pixels, is fastened to the rod 4 by an electronics card and is located at the back of said tablet 1. The card also supports a viewing target 8 and a flash 9 for obtaining better control over lighting conditions, and for revealing the corneal reflections of each eye in the images acquired by the camera 7 and visible on the screen so as to obtain better measurement accuracy. The card also carries a capacitor close to the flash 9. The capacitor is charged by means of the electronics card, which is powered by at least one universal serial bus (USB) cable, said capacitor being suitable for providing the energy needed to operate the flash 9. The capacitor has the advantage of being capable of charging the flash 9 very quickly and thus of avoiding latency times that are too long between two consecutive flashes. The tablet 1 may possess a touch screen or it may be used by means of a mouse. Said tablet 1 includes the computer and its associated software for triggering the camera, recovering images, processing said images, and displaying the results of measurements. The normal to the screen is pointed in a first direction in three dimensions, and the sighting axis of the camera 7 is pointed in a second direction that is opposite to the first direction. The camera 7 has an inclinometer enabling its angle of inclination to be determined, regardless of its orientation in three dimensions. This device 1 is compact and may easily be installed on a table or a desk. It is also configured so as to be operated by an operator, who may be an optician, seeking to measure the morpho-geometrical parameters of a person wearing eyeglasses. The person wearing eyeglasses 21 takes up a position in front of the camera 7, while the optician faces the screen of the tablet 1 and pivots the support rod 4 carrying the camera 7 so that the frame 21 and the eyes 27 on the person are properly framed on the display screen. The measurement method of the invention can then be launched. In another variant embodiment, the camera and the screen of the tablet may be placed side by side so as to enable the person wearing eyeglasses to operate the measurement method of the invention directly.

Figure 2:
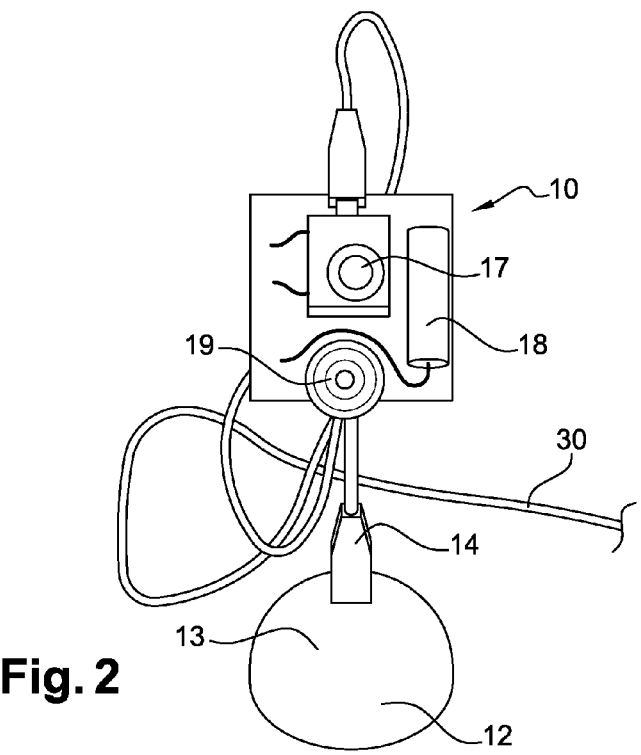
FIG. 2 is a perspective view of a second preferred embodiment of a measurement device enabling a method of the invention to be implemented.

With reference to FIG. 2, a second preferred embodiment of a measurement device 10 of the invention comprises an image acquisition system 17 in the form of a high-resolution video camera, advantageously having resolution greater than or equal to 1 million pixels. The camera 17 is carried by a support 12 having a wide stand 13 surmounted by a deformable rod 14 that is easily twisted to adopt a plurality of positions. When the stand 13 is standing on a substantially plane surface 16, the rod 14 is in a position that is inclined relative to a vertical direction to a greater or lesser extent. An electronics card that is fastened to the rod 14 supports the camera 17, a viewing target 18 for the person wearing eyeglasses 21, and a flash 19 both to obtain better control over lighting conditions and to make the corneal reflections of each eye visible in the images acquired by the camera 17 and viewable on the screen, thereby obtaining better measurement accuracy. The electronics card carries a capacitor in the vicinity of the flash 19. The capacitor is thus recharged by means of the electronics card, which is powered by at least one USB cable, said capacitor being suitable for providing the energy needed to operate the flash 19. The capacitor has the advantage of being capable of charging the flash 19 very quickly, and thus of avoiding latency times between two consecutive flashes that are too long. The camera 17 is provided with an inclinometer enabling its angle of inclination to be determined, regardless of its orientation in three dimensions. A display screen associated with a computer and located in the immediate vicinity of said camera 17 for the purpose of viewing the images acquired by said camera 17, together with the results that are obtained, is connected to the camera 17 via a data connection, e.g. such as a USB cable 30. The cable 30 serves to send to the computer the images that are obtained together with the data from the inclinometer. The computer in this embodiment provides the same features as the computer in the first embodiment. Depending on the orientation of said screen, the measurement method of the invention may be controlled either by an optician or else directly by the person wearing eyeglasses. The image acquisition device 10 is of small size and is easily installed on a table or a desk. It may even be moved on said desk, and it may be tilted to a greater or lesser extent, merely by manipulating it by hand.

Figure 7:
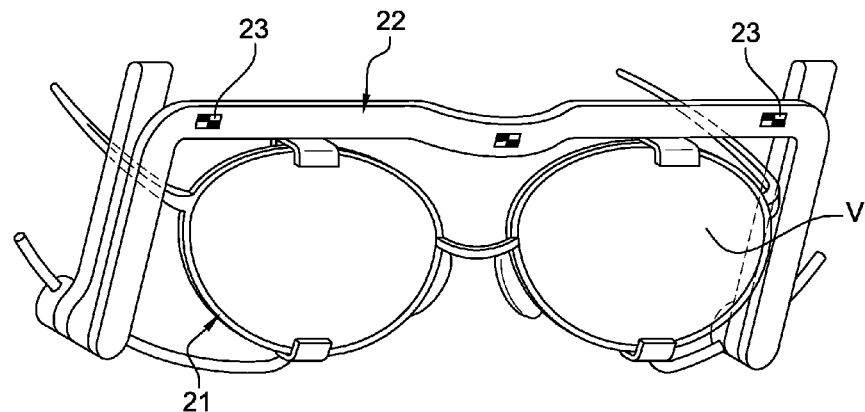
FIG. 7 is a perspective view of a pair of eyeglasses fitted with a clip possessing markers.

In the two embodiments described, the camera 7, 17 is oriented in portrait mode, thereby making it possible to cover people over a wide range of sizes without it being necessary to adjust the orientation of said camera 7, 17. Nevertheless, for unusual situations, e.g. corresponding to a person who is too tall, or who is sitting down instead of standing, or vice versa, the camera 7, 17 can be tilted to an appropriate angle so as to frame the image on the wearer's face, and the inclinometer serves to measure the corresponding angle of inclination so that it can subsequently be incorporated in the processing of the acquired images in order to correct the measurement obtained. Another variant embodiment of a method of the invention consists in using a stationary camera 7, 17, i.e. a camera that is not adjustable in angle of inclination, with it being necessary for the wearer to take on an appropriate position, e.g. by adjusting the height of a seat on which the wearer is sitting, so that the wearer's face appears centered on the screen 8. In addition to the images obtained by the cameras 7, 17, the screens also serve to display the results of measurements, and to do so in a manner that is almost instantaneous. With reference to FIG. 7, a clip 22 including markers 23 may be fastened on the eyeglass frame 21 worn by the person in order to determine the scale of the image, said markers 23 serving to identify the position and the orientation of the frame 21 in three dimensions. It is assumed that the planes of the lenses V and of the clip 22 coincide. Nevertheless, the clip 22 is not always needed. A stereoscopic measurement system using two cameras makes it possible to determine the pantoscopic angle and also the scale factor without it being necessary to make use of a clip 22.

A method of the invention implements the following steps either in the order in which they are described, or in a different order.

Figure 3:
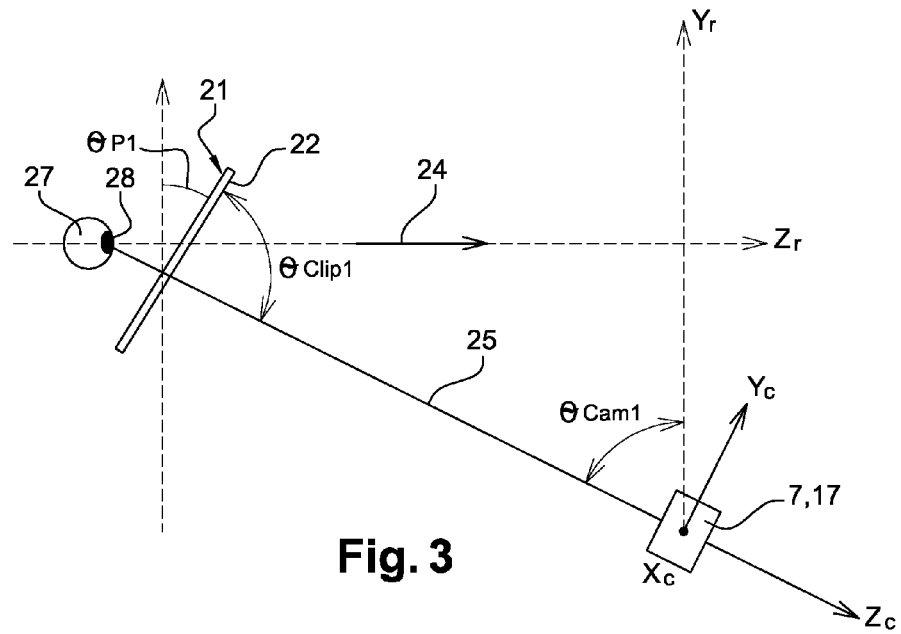
FIG. 3 is a diagrammatic profile view of a person's head in the first posture together with a camera, the person looking ahead to a point at infinity.
Figure 5:
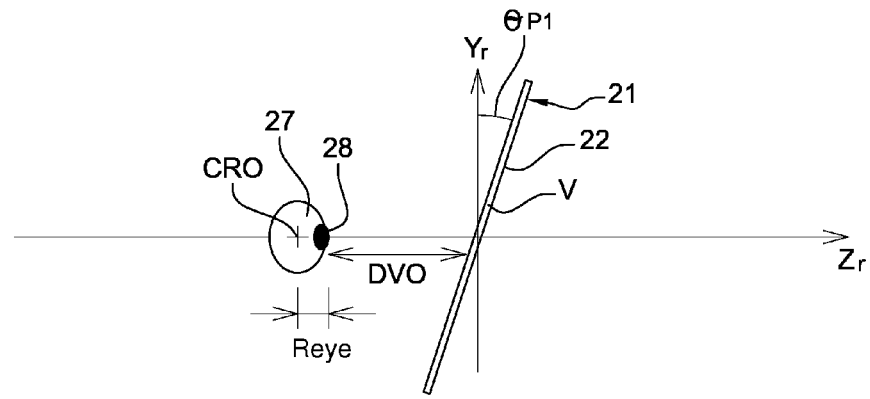
FIG. 5 is a diagrammatic profile view of a person's head in the first posture, consisting in looking ahead at a point at infinity.

With reference to FIGS. 3 and 5, the person 20 wearing eyeglasses 21 with the frame fitted with a clip 22, takes up a position in front of the camera 7, 17. The optician asks the person to adopt a first position that is comfortable and natural and that consists in looking straight ahead at a point at infinity. The gaze direction, represented by arrow 24, is then substantially horizontal. The optician adjusts the camera 7, 17 so as to see the person's face on the screen, and more particularly in a predetermined zone of said screen, by tilting the camera. 7, 17 as necessary in order to achieve this purpose.

Once the person's face is well positionet in the field of the camera 7, 17, the optician acquires a first image. The computer then determines the precise three-dimensional (3D) orientation of the clip 22 on the frame 21, and deduces therefrom a pantoscopic angle ΘP1 that is expressed as a function of the angle ΘClip1 of the clip 22 relative to the axis 25 of the camera 7, 17 and relative to the angle ΘCam1 of the camera. 7, 17 relative to the vertical, as measured with the inclinometer. The pantoscopic angle ΘP1 is measured by the clip 22 by relying on at least three markers 23 positioned on the clip 22 in relative positions that are accurately known. These markers 23 define a single plane, and the camera 7, 17 in association with image-processing software determines the 3D position of these three markers 23 in the frame of reference (Xc, Yc, Zc), and consequently determines, the orientation of said plane relative to said frame of reference. This orientation gives the angle ΘClip1 directly. The 3D coordinates of the markers 23 of the clip 22 are measured conventionally using iterative algorithms of the POSIT type. The following angular relationship is then obtained:

$$\Theta P1 = \Theta Clip1 - \Theta Cam1 \qquad 5$$

Figure 4:
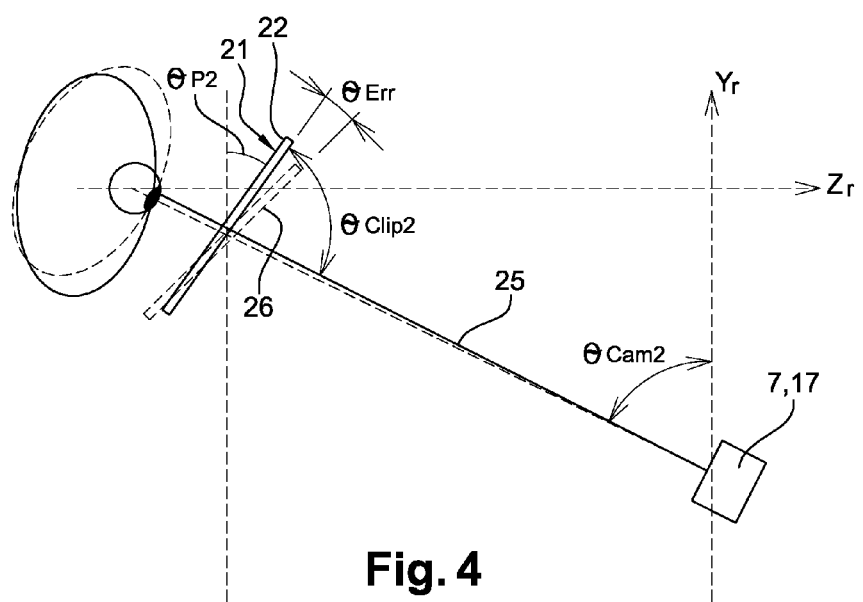
FIG. 4 is a diagrammatic profile view of a person's head in the second posture, together with a camera, the person looking at a target on said camera.
Figure 6:
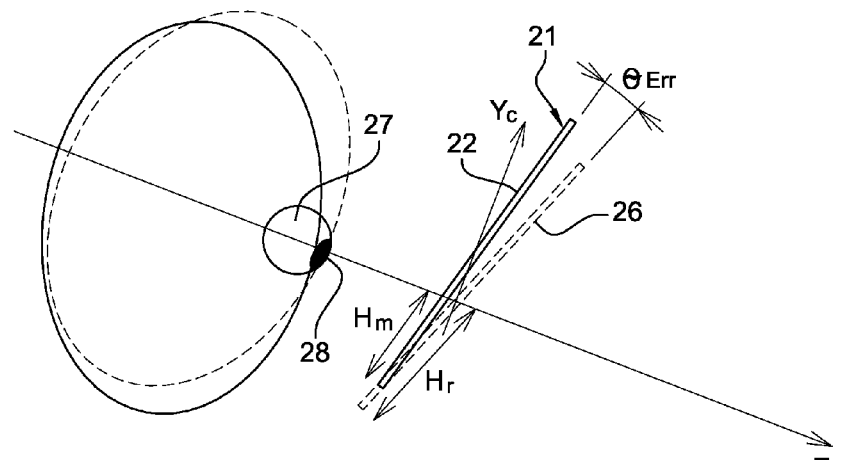
FIG. 6 is a diagrammatic profile of a person's head in the second posture, consisting in looking at a target on said camera.

With reference to FIGS. 4 and 6, the optician asks the person no adopt a second posture that is comfortable and natural, consisting in looking at the target 8, 18 placed on the camera 7, 17.

The optician acquires a second image. The pantoscopic angle $\Theta P2$ is measured once again. Ideally, the device does not move between the two postures ($\Theta Cam1 = \Theta Cam2 = \Theta Cam$) since the field of the camera is large enough to cover the movement of the head between the two positions. The flash unit 9, 19 is operated during this second image acquisition so as to obtain the corneal reflections. The corneal reflections are extracted from the image, as are the right-left bottom edges and the right left nose sides of the frame 21 so as to measure the heights (H) and the pupillary distances (½PD). The clip 22 is also used to restore the scale of the image and thus obtain correct values for H and PD. The height as measured in this example is Hm and it includes an error since the position of the head as held in the second posture is not the ideal position represented in FIGS. 4 and 6 by the clip 22 shown in dashed lines 26, i.e, the position in which the error is zero and that corresponds to the head tilting through an angle 90°−ΘCam, where ΘCam is the angle between the camera 7, 17 and the vertical. The real value Hr of the height differs from the measured height. Hm by the relationship Hr=Hm+ΔH. By way of indication, FIG. 6 shows the angle error ΘErr corresponding to the second posture, and the position of the head and of the clip 22 corresponding to a zero angle error ΘErr by dashed lines 26.

Figure 8:
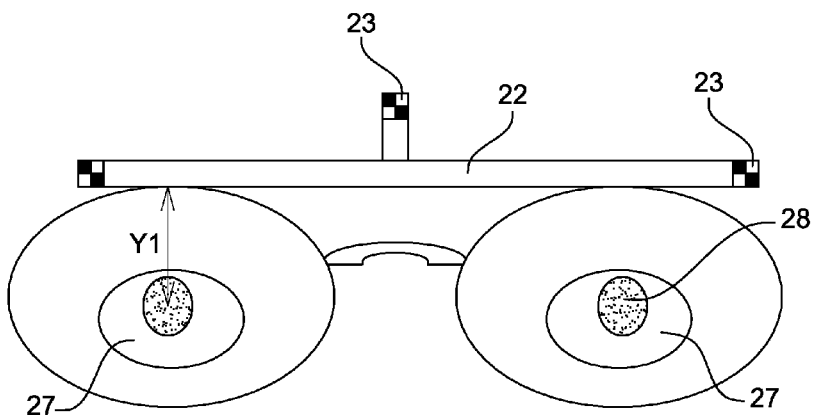
FIG. 8 is a simplified elevation view of a person's eyes and a pair of eyeglasses fitted with a marker clip, the person being in the first posture.
Figure 9:
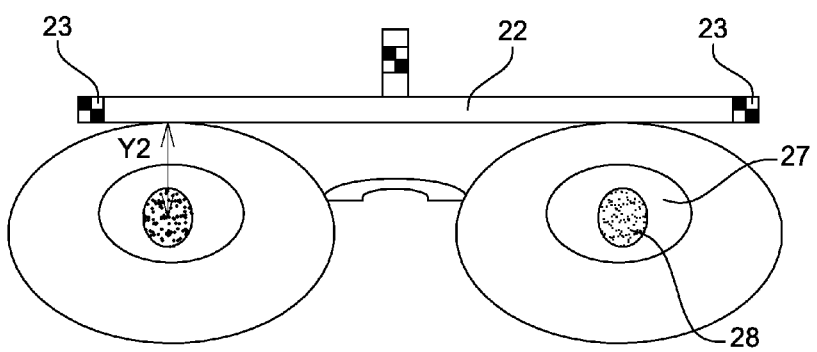
FIG. 9 is a simplified elevation view of a person's eyes and a pair of eyeglasses fitted with a marker clip, the person being in the second posture.

The errors concerning the height H are then corrected by taking account of the angle error ΘErr of the clip in the second image and of the lens-to-eye distance (DVO). The angle error is given by:

$$\Theta Err = \Theta P1 - \Theta P2 - (90° - \Theta Cam)$$

and the correction for height is given to a first approximation by:

$$\Delta H = (Reye + DVO) \times \tan(\Theta Err) = d(CRO, V) \times \tan(\Theta Err)$$

where Reye is the radius of the eye, on average equal to 12 millimeters (mm), and PVC is the lens-to-eye distance, on average equal to 15 mm. The parameter d(CRO,V) represents the distance between the center of rotation CRC of the eye and the lens V. FIG. 5 makes it possible in particular to visualize the distances and the parameters represented by DVO, CRO, and Reye, with reference to the position of the lens V, i.e. the position of the frame 21 or of the clip 22, and also to the positions of the eyes 27 and of the pupils 28. With reference to FIGS. 7, 8, and 9, in order to obtain better accuracy, the exact value of DVO may be measured using the images corresponding to the two postures. To do this, the two images are used and the posture of the clip 22 as obtained using the markers 23 is extracted, as are the positions of the eyes 27, e.g. by identifying the pupils 28, the irises, or the corners of the eyes.

The positions of the pupil 28 and/or of the iris of each of the two eyes 27 in the plane of the clip 22 for the two images is determined by projecting the pupil 28 into the frame of reference of the clip 22, and using triangulation to deduce therefrom the position of the CRO of each of the two eyes 27 in the frame of reference of the clip 22. This gives:

$$d(CRC, V) = (Y1 - Y2) / \tan(\Theta P1 - \Theta P2)$$

If use is made of the corners of the eyes 27, then:

$$DVO = (Y1 - Y2) / \tan(\Theta P1 - \Theta P2)$$

where Y1 and Y2 are the coordinates of the corners of the eye.

In arbitrary manner, it is possible to consider taking a mean value for the distance between CRC and V, which value may for example be 27 mm. In a first alternative, it is possible to ask the wearer, while taking the second image, to tilt the head further so as to obtain an angle difference of at least 10°.

In a second alternative, it is possible to ask the person to turn the head without gazing on the target 8, 18 or on any particular item, and to measure DVO by using the corners of the eyes 27.

When the wearer of the eyeglasses 21 does not tilt the head between taking the two images, then $\Theta P1 = \Theta P2$.

The pupillary distance or half-distance PD, the height H between the pupil 28 of the eye 27 and the bottom edge of the lens V or of the frame 21, the distance DVO between the eye 27 and the lens V, and the pantoscopic angle ΘP are the main morpho-geometrical parameters that can be determined using a measurement method of the invention.

The positions of the pupils 28, of the irises, of the corneal reflections, and of the corners of the eyes are determined by the operator by pointing manually on an acquired image, or by the computer performing automatic detection on the two acquired images.

The iris, the corneal reflections, and the pupils are elements that present the advantage of being less masked by the frame while the person is tilting the head than the corners of the eyes. Furthermore, manual pointing or automatic detection on the images of said elements is more accurate since the elements are more easily identified.

Unlike the corners of the eyes, the eyes 27 present rotary movement and are movable in the frame of reference of the clip 22. It is possible to compensate the movement of an eye between two images so as to return under such circumstances to the situation in which the eyes have not moved relative to the clip. Thus, by compensating for the positions of the eyes 27 in the second image by a distance dP, the situation returns to that in which the item has not moved relative to the clip 22. To a first approximation dP is substantially equal to the distance through which the pupil 28 or the iris or the corneal reflection moves in translation between the two images. A more accurate geometrical calculation may be implemented by taking account of the radius of the eye 27, the angle between the camera and the horizon, the variation in the angle of the clip 22 between the two images, and the variation in the angle of the eye between the two images.

In addition, geometrical compensation associated with the fact that the iris is not in the same plane as the top of the cornea may advantageously be taken into account using conventional trignometrical relationships. Preferably, geometrical compensation for a convergence defect associated with the fact that the person's eyes 27 are not looking at the acquisition system. 7, 17 but at the top of the camera lens can also be incorporated in the calculations so as to diminish potential sources of inaccuracy concerning the parameters determined using a method of the invention.

The invention claimed is:

1. A measurement method for measuring morpho-geometrical parameters of a person wearing eyeglasses, said method implementing an independent computer device having a screen, a target, a compact image acquisition system including means for determining its angle of inclination, said system being connected to said screen, and a computer enabling the image acquisition system to be controlled and enabling the images obtained to be processed, said method comprises the steps of:
   causing the person to observe a point situated in front and at infinity while holding the head naturally in a substantially horizontal direction, the pair of eyeglasses occupying a natural position on the person's face;
   acquiring a first image of the position of the frame in this first posture;
   causing the person to tilt their to observe the target placed in a known position relative to the image acquisition system other than said point from said first image, where said person continues to adopt a position that is natural and comfortable, the pair of eyeglasses conserving an unchanged position on the person's face relative to the first posture;
   acquiring a second image of the position of the frame in this second posture, by means of the same image acquisition system as was used for the first posture;
   determining the positions of the eyes from one of the two images;
   computer processing of the two images obtained in order to determine the morpho-geometrical parameters of the person from the positions of the eyes, from the position of the frame in the first posture, from the position of the frame in the second posture, and from the angle of inclination of the image acquisition system, said processing including a calculation correction to take account of a difference in inclination of the plane of the person's face relative to the gaze axis from the eyes to the gaze point, between the first and second positions; and
   providing the results of the measurements.

2. A measurement method according to claim 1, wherein the frame is fitted with position-identification means in the form of a clip provided with markers and fastened on said frame, and in that the angle of inclination of said frame is evaluated from a single camera.

3. A measurement method according to claim 1, wherein the angle of inclination of the frame is evaluated by means of at least one camera used in a stereoscopic method, said camera taking two images.

4. A measurement method according to claim 3, wherein the angle of inclination of the frame is evaluated by means of at least two cameras used in a stereoscopic method.

5. A method according to claim 1, wherein the image acquisition system is a high-resolution camera.

6. A method according to claim 1, wherein the means for determining the angle of inclination of the acquisition system comprise an inclinometer.

7. A method according to claim 1, wherein the morpho-geometrical parameters measured by said method are the height H between the pupil and the bottom rim of the lens (V), and the pantoscopic angle $\Theta P$.

8. A method according to claim 7, wherein the measured height Hm is corrected in order to take account of the distance DVO between the lens (V) and the eye.

9. A method according to claim 8, wherein the distance DVO between the lens (V) and the eye is deduced from a measurement of disparities between the two images.

10. A method according to claim 1, wherein an operator is placed in front of the person wearing eyeglasses, said operator adjusting the image acquisition system and controlling the various steps of said method.

11. A method according to claim 1, wherein the acquisition system is adjusted in angle of inclination in order to adapt to the position of the person's face.

12. A method according to claim 1, wherein the angle of inclination of the acquisition system is constant, the person positioning the face at the appropriate height for causing it to appear in the center of the image.

13. A measurement device for implementing a measurement method according to claim 1, wherein the device comprises:
   a computer;
   at least one camera fitted with an inclinometer; and
   a display screen enabling the images taken by said camera to be viewed together with the results of the measurements, it being possible for the position of the camera and the position of the screen to be adjusted independently of each other.

14. A measurement device according to claim 13, wherein said device is constituted by a tablet combining the screen, a secondary camera, the inclinometer, and the computer, and also by said at least one camera.

15. A measurement device according to claim 14, wherein said device includes a support on which the tablet and the camera are fastened.

16. A measurement device according to claim 15, wherein the camera and the tablet are situated on either side of a vertical plane and form between them an angle lying in the range 15° to 45°.

* * * * *